United States Patent [19]

Stern

[11] 4,400,386
[45] Aug. 23, 1983

[54] ANTIMICROBIAL DERIVATIVES OF 8-AMINO AND 8-AMINOMETHYL BENZO(IJ)QUINOLIZINE

[75] Inventor: Richard M. Stern, Cottage Grove, Minn.

[73] Assignee: Riker Laboratories, Inc., St. Paul, Minn.

[21] Appl. No.: 318,930

[22] Filed: Nov. 6, 1981

[51] Int. Cl.³ .................... A61K 31/47; A01N 43/90; C07D 455/04
[52] U.S. Cl. .................................... 424/258; 546/94; 546/165
[58] Field of Search .......................... 546/94; 424/258

[56] References Cited

U.S. PATENT DOCUMENTS

| | | | |
|---|---|---|---|
| 3,896,131 | 7/1975 | Gerster | 546/94 |
| 3,917,608 | 11/1975 | Ellis et al. | 546/94 |
| 3,976,651 | 8/1976 | Gerster et al. | 546/94 X |
| 3,985,753 | 10/1976 | Schuppan et al. | 546/94 |
| 3,985,882 | 10/1976 | Gerster | 424/258 |

FOREIGN PATENT DOCUMENTS

| | | | |
|---|---|---|---|
| 55-27204 | 9/1980 | Japan | 546/94 |
| 55-131632 | 9/1980 | Japan | 546/94 |
| 55-59121 | 11/1980 | Japan | 546/94 |
| 55-61776 | 11/1980 | Japan | 546/94 |
| 55-106776 | 12/1980 | Japan | 546/94 |
| 56-131630 | 2/1981 | Japan | 546/94 |
| 56-131629 | 5/1981 | Japan | 546/94 |
| 56-131631 | 5/1981 | Japan | 546/94 |
| 56-135807 | 5/1981 | Japan | 546/94 |

Primary Examiner—Richard A. Schwartz
Attorney, Agent, or Firm—Cruzan Alexander; Donald M. Sell; Carolyn A. Bates

[57] ABSTRACT

This invention relates to antimicrobial compounds of the formula

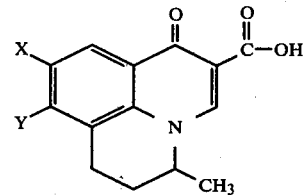

wherein X is hydrogen or fluorine; Y is selected from the group consisting of

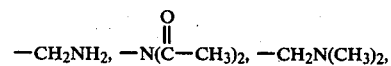

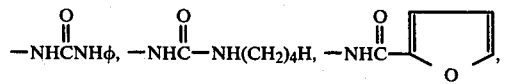

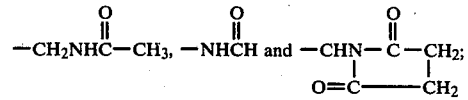

and ester, carboxylate salts, and alkylaminoalkyl ester salts thereof.

5 Claims, No Drawings

ANTIMICROBIAL DERIVATIVES OF 8-AMINO AND 8-AMINOMETHYL BENZO(IJ)QUINOLIZINE

TECHNICAL FIELD

This invention relates to derivatives of the heterocyclic system known as benzo[ij]quinolizine. More specifically, it relates to substituted 6,7-dihydro-5-methyl-1-oxo-1H,5H-benzo[ij]quinolizine-2-carboxylic acids and esters and salts thereof. The use of these compounds as antimicrobial agents and pharmaceutical compositions containing the compounds are also included within the scope of the invention.

BACKGROUND ART

U.S. Pat. Nos. 3,896,131 and 3,985,882 describe substituted 6,7-dihydro-5-methyl-1-oxo-1H,5H-benzo[ij]-quinolizine-2-carboxylic acids which are useful antimicrobial agents. Those patents describe compounds which may be substituted in the 8, 9 or 10 position by a number of substituents including amio ($-NH_2$), N,N-dialkylamino [$(CH_3)_2N-$], lower alkanamido and trifluoroacetamido groups. The present invention relates to compounds containing more complex nitrogen-containing substituents than those described in the aforementioned patents and specifically in the 8-position. It also relates to novel compounds which start with a non-aromatic aminomethyl group ($NH_2CH_2-$) in the 8-position and provide further derivatives.

DETAILED DESCRIPTION OF THE INVENTION

This invention relates to substituted 6,7-dihydro-5-methyl-1-oxo-1H,5H-benzo[ij]quinolizine-2-carboxylic acids of the formula

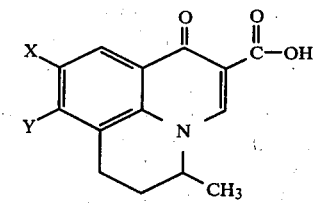

(Formula I)

wherein X is hydrogen or fluorine; Y is selected from the group consisting of

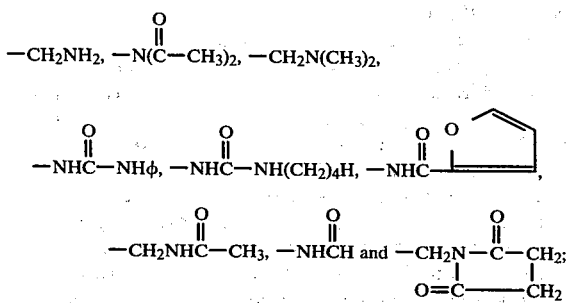

and esters, carboxylate salts and alkylaminoalkyl ester salts thereof.

Compounds of the invention have an optically active carbon at the 5-position. All such optical isomers are included within the scope of the invention.

It is well known to the art that pharmaceutically-acceptable salts such as alkali metal, alkaline earth, aluminum, iron and other metal and amine salts of pharmaceutically active acids are the equivalents of the acids, and in some cases may even offer advantages in absorption, formulation and the like. Salts of the free acid compounds of the invention are readily prepared by reaction of the acid with a base and evaporation to dryness. The base may be organic, e.g., sodium methoxide or an amine, or inorganic, e.g., sodium hydroxide.

Esters of the acid compounds of the invention may be obtained as intermediates during the preparation of the acidic compounds, in some cases, or the esters may be prepared directly using standard synthetic methods. These esters exhibit antimicrobial activity but are primarily of interest as synthetic intermediates, although in some instances hydrolyzable or salt-forming esters may be of interest as therapeutic agents. Preferred esters of the compounds of the invention are alkyl esters and alkylaminoalkyl esters having one to four carbon atoms in the alkyl group. Especially preferred are alkylaminoalkyl esters which will form salts, e.g., hydrochlorides, such as the dimethylaminoethyl esters.

The esters are readily prepared by reacting the free acid of Formula I with thionyl chloride to provide the novel acyl chloride derivative. The acyl chloride is reacted with the appropriate alcohol to provide the desired ester.

The antimicrobial activity of the compounds of the present invention can be demonstrated by the known, standard plate dilution method for testing bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 5 g. |
| Sodium chloride | 5 g. |
| Oxoid agar-agar No. 3 | 15 g. |
| Water | 1 liter |

Using this test, compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound which gives complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are inoculated onto the agar plates containing the various compound concentrations. The plates are incubated at 37° C. in a 10 percent carbon dioxide atmosphere for 18–24 hours. The microbial growth on each plate is read visually, and minimal inhibitory concentrations are recorded. Some of the microorganisms which are used for this test are:

1. *Staphylococcus aureus*
2. *Bacillus subtilis*
3. *Escherichia coli*
4. *Pseudomonas aeruginosa*
5. *Streptococcus sp.* *
6. *Asperigillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*Strains isolated from dental caries in rats or hamsters at the National Institute of Dental Health and grown in PFY or APT agar.

All of the compounds of the invention possess antimicrobial activity against one or more of the above microorganisms.

Some of the compounds of the invention have also shown activity against one or more anaerobic bacteria, for example Bacteroides sp. and *Clostridium welchii*. Some compounds of the invention have shown useful activity toward Erwinia amylovora, a gram-negative microorganism responsible for the plant disease known as fire blight.

It will be understood by those skilled in the art that the species used are representative indicator species, as it would be impractical to screen against all microorganisms. It is well known in the art that broad spectrum activity can be predicted on the basis of activity shown against selected representative species of microorganisms.

Some of the compounds of the invention are active when administered orally to animals. They are excreted in the urine, and are effective urinary tract antibacterials in mammals. They are also contemplated for use in the treatment of pulmonary infections, soft tissue infections, burn infections and bacteremias.

All of the compounds of the invention are active against microorganisms in virto or topically. In vitro activity is useful in itself, since antimicrobial agents may be used for disinfecting and sterilizing, e.g., medical and dental equipment, as components of disinfecting solutions.

The acute oral toxicity of the compounds of the invention generally is moderate to low compared with the effective oral dose, and they have an acceptable therapeutic ratio.

Presently preferred compounds due to their broad spectrum antimicrobial activity are those selected from the group consisting of: (1) the compound wherein X is hydrogen and Y is

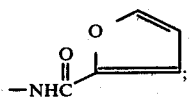

(2) the compound wherein X is hydrogen and Y is —CH$_2$NH$_2$; (3) the compound wherein X is hydrogen and Y is

(4) the compound wherein X is fluoro and Y is

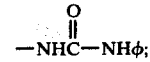

(5) the compound wherein X is fluoro and Y is

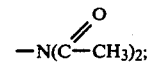

(6) the compound wherein X is hydrogen and Y is —CH$_2$N(CH$_3$)$_2$; and (7) the compound wherein X is fluoro and Y is

The acidic compounds of the invention are ordinarily white or yellowish crystalline or amorphous materials when purified. They are substantially insoluble in water, lower alcohols or hydrocarbons and are more soluble in halogenated solvents, dimethylformamide and the like. The esters are generally somewhat more soluble in organic solvents. The salts, especially the alkali metal salts, have appreciable solubility in water and lower alcohols.

The compounds of the invention may be formulated by incorporating them into conventional pharmaceutical vehicles, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of a compound used to treat, e.g., a microbial urinary infection by oral administration will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of conventional pharmaceutical preparations such as capsules, tablets, emulsions, solutions and the like. Excipients, fillers, coatings, etc. are generally employed with tablets or capsules, as is well known in the art.

It is known to the art that antimicrobial agents are used as growth promoters in various animal and bird species. Although not yet verified, it is inferred from their outstanding antimicrobial activity that the compounds of the invention can be used for this purpose also. The compounds of the invention may also be used for the control of microbial (e.g., *Erwinia amylovora*) infections of plants, e.g., by spraying or dusting formulation of these compounds on the affected area.

The compounds of the invention are prepared starting with known compounds to make the key intermediates 8-amino-6,7-dihydro-9-fluoro-5-methyl-1-oxo-1H,5H-benzo[ij]quinolizine-2-carboxylic acid and 8-amino-6,7-dihydro-5-methyl-1-oxo-1H,5H-benzo[ij]quinolizine-2-carboxylic acid.

The 9-fluoro-substituted compounds start with the known compound 6-fluoroquinaldine which is nitrated with fuming nitric and sulfuric acids in the presence of sodium nitrite catalyst to provide the compound 6-fluoro-5-nitroquinaldine.

The nitro group is reduced catalytically, for example, in the presence of palladium on charcoal. If this reaction is carried out in the presence of acetic anhydride, the product is the compound 5-acetamido-6-fluoroquinaldine. This intermediate is further reduced catalytically in the presence of platinum on charcoal to provide the compound 5-acetamido-6-fluorotetrahydroquinaldine.

The tetrahydroquinaldine intermediate is condensed with diethyl ethoxymethylenemalonate by heating without solvent at 100°–200° C. for several hours (preferably 140°–150° C. for two hours). The intermediate formed is the compound of the formula

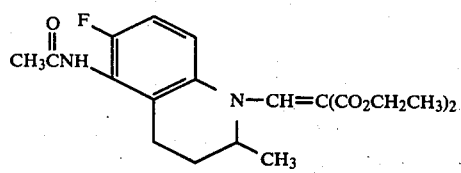

Formula II

This intermediate is an oil which need not be isolated or purified. Instead, polyphosphoric acid is added and the solution is heated at 100°–140° C. to effect a condensation to provide an ester of the acids of Formula I wherein Y is acetamido. The next step is saponification of the ester and hydrolysis of the acetamido group to provide 8-amino-6,7-dihydro-9-fluoro-5-methyl-1-oxo-1H,5H-benzo[ij]quinolizine-2-carboxylic acid, a key intermediate.

Compounds of the invention wherein X is hydrogen are prepared from 5-aminoquinaldine by blocking the amio group as acetamido and converting to 8-acetamido-6,7-dihydro-5-methyl-1-oxo-1H,5H-benzo[ij]quinolizine-2-carboxylic acid as outlined above. This intermediate is then hydrolyzed to the 8-amino compound.

The 8-ureido compounds of the invention, i.e., where Y is

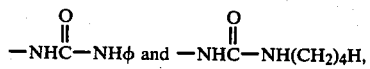

are prepared by reacting the appropriate 8-amino compounds with phenyl and butyl isocyanates, respectively. The 8-amino compounds also react with furoyl chloride to form the corresponding amides, i.e., where Y is

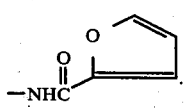

The 8-amino compounds may be reacted with acetic anhydride or alkanoyl chlorides such as acetyl chloride or other anhydrides to form 8-acetamido and other 8-alkanamido derivatives. The 8-(diacetyl)imido compounds of the invention, i.e., where Y is

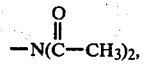

are formed by reacting 8-acetamido with excess acetic anhydride. The 8-amino compound will form 8-formamido compounds, i.e., where Y is

by reaction with formic acid in acetic anhydride.

Compounds of the invention where Y is —CH$_2$NH$_2$(aminomethyl), —CH$_2$N(CH$_3$)$_2$ (N,N-dimethylaminomethyl),

(acetamidomethyl), and

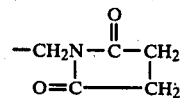

(succinimidomethyl) are derived from the corresponding 8-cyano intermediates directly, or, in some cases, by first preparing the 8-acetamidomethyl or the 8-aminomethyl compounds. For example, succinic anhydride can be reacted with the 8-aminomethyl group to form the 8-succinimidomethyl compounds, and the N-N-dimethylaminomethyl compounds are formed by reductive alkylation of the 8-aminomethyl group.

The 8-cyano intermediate wherein X is hydrogen is prepared from the 8-amino intermediate by diazotization in the presence of fluoroboric acid, followed by isolation of the fluoroborate salt and heating of the fluoroborate salt in the presence of a cyanide salt (preferably cuprous cyanide) in a very polar solvent such as dimethyl sulfoxide.

In order to prepare the intermediate 8-cyano-6,7-dihydro-9-fluoro-5-methyl-1-oxo-1H,5H-benzo[ij]-quinolizine-2-carboxylic acid, one starts with 2-fluorobenzoic acid and nitrates. Nitration with concentrated nitric and concentrated sulfuric acids at moderate temperatures (15°–25° C.) provides 2-fluoro-5-nitrobenzoic acid. Catalytic reduction e.g., with palladium on charcoal catalyst, provides 5-amino-2-fluorobenzoic acid. Condensation of this aromatic amine with crotonaldehyde in the presence of ferrous sulfate heptahydrate and sodium m-nitrobenzenesulfonate provides 5-carboxyl-6-fluoroquinaldine. The carboxyl group is reacted with thionyl chloride to provide the carboxyl chloride which is reacted with ammonium hydroxide to provide 5-carboxamido-6-fluoroquinaldine. Dehydration of the carboxamido group in pyridine with trifluoroacetic anhydride in an inert solvent such as dichloromethane provides 5-cyano-6-fluoroquinaldine. This intermediate condenses with diethyl ethoxymethylenemalonate to yield an intermediate of Formula II where the 5-position is substituted by cyano. Condensation in polyphosphoric acid provides the benzo[ij]quinolizine ring, but the cyano group may be partially hydrolyzed and again require dehydration with pyridine and trifluoroacetic anhydride. Hydrolysis of the carboxylic ester group in the 2-position may also be required to obtain the desired intermediate.

The 8-cyano intermediate wherein X is hydrogen may also be prepared by the foregoing synthetic route starting with the known compound 5-carboxylquinaldine. It has now been found that this is the preferred synthetic route for preparing both 8-cyano intermediates.

The following examples are provided to illustrate the synthetic methods useful to obtain compounds of the invention, and are not intended to be limiting of the invention.

EXAMPLE 1

Part A. Preparation of 6-Fluoro-5-nitroquinaldine

To 3.5 l of fuming sulfuric acid was added, with cooling, 600 g (3.73 moles) of 6-fluoroquinaldine in small portions. About 0.1 g of sodium nitrate was added to the mixture, followed by the dropwise addition of 261 ml of fuming red nitric acid over a six-hour period while maintaining the temperature at 5°–10° C. The mixture was stirred at 20° C. for sixteen hours, then poured into 3 gallons of ice. The mixture was basified with ammonium hydroxide with cooling. The precipitated solid was separated by filtration and dissolved in about two liters of warm toluene. The solution was dried over magnesium sulfate, filtered and evaporated to provide a yellow solid, 6-fluoro-5-nitroquinaldine, m.p. 105°–108° C., which was recrystallized from 1,2-dichloroethane. The structural assignment was confirmed by nuclear magnetic resonance and infrared spectral analyses.

Part B. Separation of 5-Acetamido-6-fluoroquinaldine

To a mixture of 20 g (0.1 mole) of 6-fluoro-5-nitroquinaldine in 180 ml of ethyl acetate and 20 ml of acetic anhydride was added 3 g of ten percent palladium on charcoal. The mixture was hydrogenated with hydrogen gas at 50 psi on a Paar apparatus for 20 minutes. The theoretical amount of hydrogen (25 psi) was used. On cooling, the mixture solidified to a yellow mass. About 200 ml of ethanol was added, and the mixture was heated to dissolve the product. The catalyst was filtered off through celite, and the filtrate was evaporated to dryness, leaving a yellow solid. The solid was triturated with 200 ml of water and neutralized with ten percent sodium hydroxide solution. Filtration and drying provided white crystals of 5-acetamido-6-fluoroquinaldine, m.p. 232°–235° C. The structural assignment was confirmed by infrared spectral analysis.

Part C. Preparation of 5-Acetamido-6-fluorotetrahydroquinone

In one liter of acetic acid was dissolved 95 g of 5-acetamido-6-fluoroquinaldine. To this mixture was added 10 g of five percent platinum on charcoal. The mixture was hydrogenated with hydrogen gas at 30 psi on a Paar apparatus for five hours. The amount of hydrogen used was 61 psi (versus 62 psi theoretical). The catalyst was removed by filtration, the filtrate was concentrated to 250 ml and decanted into cold stirred sodium hydroxide solution. The white precipitate was separated by filtration and triturated with a chloroform/hexane (50/50) mixture to provide white crystals of 5-acetamido-6-fluorotetrahydroquinaldine, m.p. 168°–170° C. The structural assignment was confirmed by infrared spectral analysis.

Part D. Preparation of Diethyl 2-[N-(5-Acetamido-6-fluorotetrahydroquinaldinyl)]methylenemalonate A mixture of 6.4 g (28.8 mmole) of 5-acetamido-6-fluorotetrahydroquinaldine and 8 g (37 mmole) of diethyl ethoxymethylenemalonate was heated at 140°–150° C., with stirring, for two hours. Ethanol was allowed to evolve. The product, diethyl 2-[N-(5-acetamido-6-fluorotetrahydroquinaldinyl)]methylenemalonate, was not isolated.

Part E. Preparation of 8-Amino-6,7-dihydro-9-fluoro-5-methyl-1-oxo-1H,5H-benzo[ij]quinolizine-2-carboxylic Acid The reaction mixture of part D. containing diethyl 2-[N-(5-acetamido-6-fluorotetrahydroquinaldinyl)]methylenemalonate was treated with 25 g of polyphosphoric acid and warmed to 100° C. for 5 minutes while stirring. Foaming was observed, demonstrating that the reaction had commenced. The external heating was removed, and stirring was continued for ten minutes. Heat was reapplied and the mixture was maintained at 100° C. for 0.5 hour. The cyclized product was then hydrolyzed (ester portion) and deacetylated (acetamido group) by adding 150 ml of water and 25 ml of methanol, basifying cautiously with fifty percent sodium hydroxide solution and heating at reflux for 2.5 hours. Filtration through decolorizing charcoal and celite and decantation into rapidly stirring dilute acetic acid provided a tan solid, hydrated 8-amino-6,7-dihydro-9-fluoro-5-methyl-1-oxo-1H,5H-benzo[ij]quinolizine-2-carboxylic acid, m.p. 300° C. Analysis: Calculated for $C_{14}H_{13}FN_2O.1/3H_2O$; %C, 59.5; %H, 4.8; %N, 9.9; Found: %C, 59.1; %H, 4.5; %N, 9.8.

EXAMPLE 2

Using the method of Example 1 and starting with the known compound 5-acetamidoquinaldine, 8-amino-6,7-dihydro-5-methyl-oxo-1-1H,5H,benzo[ij]quinolizine-2-carboxylic acid hydrate, m.p. 238°–240° C. was obtained. Analysis: Calculated for $C_{14}H_{14}N_2O_3.H_2O$: %C, 60.9; %H, 5.8; %N, 10.1; Found: %C, 61.2; %H, 5.9; %N, 10.3.

EXAMPLE 3

A solution of 2.0 g of 8-amino-6,7-dihydro-5-methyl-1-oxo-1H,5H-benzo[ij]quinolizine-2-carboxylic acid in 25 ml of glacial acetic acid was formed by heating the ingredients on a steam bath. Phenyl isocyanate (2 ml) was added to the solution, and heating was continued for about ten minutes. The hot solution was filtered. On cooling, a precipitate was obtained which was recrystallized from aqueous N,N-dimethylformamide to provide 6,7-dihydro-5-methyl-1-oxo-8-phenylureido-1H,5-benzo[ij]quinolizine-2-carboxylic acid, m.p. 282° C. (dec). Analysis: Calculated for $C_{21}H_{19}N_3O_4$: %C, 66.8; %H, 5.1; %N, 11.1; Found: %C, 66.9; %H, 5.1; %N, 11.2. The structural assignment was confirmed by infrared and nuclear magnetic resonance spectral analyses.

EXAMPLE 4

Following the method of Example 3 and reacting the 8-amino-6,7-dihydro-5-methyl-1-oxo-1H,5H-benzo[ij]quinolizine-2-carboxylic acid with n-butyl isocyanate, the twice-recrystallized product was white crystals of 8-n-butylureido-6,7-dihydro-5-methyl-1-oxo-1H,5H-benzo[ij]quinolizine-2-carboxylic acid, m.p. 225° C. (dec.). Analysis: Calculated for $C_{19}H_{23}N_3O_4$: %C, 63.8; %H, 6.5; %N, 11.7; Found: %C, 63.8; %H, 6.4; %N, 11.7.

EXAMPLE 5

A solution of 2.0 g of 8-amino-6,7-dihydro-5-methyl-1-oxo-1H,5H-benzo[ij]quinolizine-2-carboxylic acid in 25 ml of glacial acetic acid was prepared by heating the mixture on a steam bath. To this mixture was added 2 ml of 2-furoyl chloride, and heating was continued for 30 minutes. After cooling at 20° C. for two hours, the mixture was heated at 100° C., and 15 ml of water was added. Cooling provided a solid which was recrystallized from aqueous N,N-dimethylformamide to provide white crystals of 6,7-dihydro-8-(2-furamido)-5-methyl-1-oxo-1H,5H-benzo[ij]quinolizine-2-carboxylic acid, m.p. 278°–279° C. Analysis: Calculated for $C_{19}H_{16}N_2O_5$: %C, 64.8, %H, 4.6; %N, 7.9; Found: %C, 64.7; %H, 4.5; %N, 7.8. The structural assignment was confirmed by infrared and nuclear magnetic resonance spectral analyses.

EXAMPLE 6

Part A

A mixture of 0.0037 mole (1.0 g) of 8-cyano-6,7-dihydro-5-methyl-1-oxo-1H,5H-benzo[ij]quinolizine-2-carboxylic acid (see Example 14 below), 10 ml of thionyl chloride and 1 drop N,N-dimethylformamide was heated at its reflux temperature for 15 minutes, then evaporated to dryness. The product was 8-cyano-6,7-dihydro-5-methyl-1-oxo-1H,5H-benzo[ij]quinolizine-2-carboxyl chloride, a gray solid.

Part B

To the product of Part A was added 25 ml of ethanol, and the mixture was heated on a steam bath for about one hour. The solvent was evaporated to provide a residue which was recrystallized from ethanol to produce ethyl 8-cyano-6,7-dihydro-5-methyl-1-oxo-1H,5H-benzo[ij]quinolizine-2-carboxylate, m.p. 249°–251° C. Analysis: Calculated for $C_{17}H_{16}N_2O_3$: %C, 68.9; %H, 5.4; %N, 9.4; Found: %C, 69.0; %H, 5.4; %N, 9.2.

Part C

A mixture of 5.0 g (16.9 mmole) of ethyl 8-cyano-6,7-dihydro-5-methyl-1-oxo-1H,5H-benzo[ij]quinolizine-2-carboxylate, 10 g of sodium acetate, 2 g of Raney nickel and 100 ml of acetic anhydride was stirred under hydrogen gas on a Paar apparatus at 50 psi and 50° C. for six hours. The catalyst was removed by filtration, and the filtrate was evaporated. The residue was dissolved in isopropyl alcohol and slowly crystallized to provide white crystals of ethyl 8-acetamidomethyl-6,7-dihydro-5-methyl-1-oxo-1H,5H-benzo[ij]quinolizine-2-carboxylate. The structural assignment was supported by infrared spectral analysis.

EXAMPLE 7

The product ethyl 8-acetamidomethyl-6,7-dihydro-5-methyl-1-oxo-1H,5H-benzo[ij]quinolizine-2-carboxylate (1.0 g) from Example 6 was mixed with 25 ml of 6 N hydrochloric acid, and the mixture was heated at reflux for two hours. The mixture was evaporated to dryness, and the residue was triturated with isopropyl alcohol. The solid obtained was dissolved in 20 ml of water. One gram of sodium acetate was added, and the mixture was treated with decolorizing charcoal and filtered. The volume of the solution was reduced to 5 ml, and 5 ml of isopropyl alcohol was added. Seeding was used to provide white crystals of 8-aminomethyl-6,7-dihydro-5-methyl-1-oxo-1H,5H-benzo[ij]quinolizine-2-carboxylic acid hydrate, m.p. 228°–250° C. (dec.). Analysis: Calculated for $C_{15}H_{16}N_2O_3 \cdot \frac{1}{2}H_2O$: %C, 64.0; %H, 6.1; %N, 10.0; Found: %C, 63.9, %H, 5.9; %N, 9.7. The structural assignment was confirmed by infrared and nuclear magnetic resonance spectral analyses.

EXAMPLE 8

A solution of 2.0 g of ethyl 8-acetamidomethyl-6,7-dihydro-5-methyl-1-oxo-1H,5H-benzo[ij]quinolizine-2-carboxylate from Example 6 was obtained by heating in 45 ml of water and 5 ml of methanol. The solution (at 20° C.) was treated with 10 ml of ten percent sodium hydroxide solution. After 72 hours the mixture was filtered, the filtrate was acidified to pH 4 with glacial acetic acid and seeded to facilitate precipitation. The product was white needles of 8-acetamidomethyl-6,7-dihydro-5-methyl-1-oxo-1H,5H-benzo[ij]quinolizine-2-carboxylic acid, m.p. 232°–234° C. Analysis: Calculated for $C_{17}H_{18}N_2O_4$: %C, 65.2; %H, 5.8; %N, 8.9; Found: %C, 65.2; %H, 5.7; %N, 8.7. The structural assignment was confirmed by infrared and nuclear magnetic resonance spectral analyses.

EXAMPLE 9

Following the method of Example 3, 1.0 g of 8-amino-6,7-dihydro-9-fluoro-5-methyl-1-oxo-1H,5H-benzo[ij]quinolizine-2-carboxylic acid was reacted with 1.0 ml of phenyl isocyanate, and the product obtained was 6,7-dihydro-9-fluoro-5-methyl-1-oxo-8-phenylureido-1H,5H-benzo[ij]quinolizine-2-carboxylic acid, m.p. 255° C. (dec.). Analysis: Calculated for $C_{21}H_{18}FN_3O_4$: %C, 63.8, %H, 4.6; %N, 10.6; Found: %C, 63.4; %H, 4.4; %N, 10.6. The structural assignment was confirmed by infrared and nuclear magnetic resonance spectral analysis.

EXAMPLE 10

A mixture of 1 g of 8-acetamido-6,7-dihydro-9-fluoro-5-methyl-1-oxo-1H,5H-benzo[ij]quinolizine-2-carboxylic acid (crude, partly free amine) and 25 ml of acetic anhydride was heated at reflux for about 30 minutes. Evaporation to dryness provided a residue which was recrystallized from aqueous N,N-dimethylformamide with 2 drops of 3 N hydrochloric acid. The first crop was 8-diacetimido-6,7-dihydro-9-fluoro-5-methyl-1-oxo-1H,5H-benzo[ij]quinolizine-2-carboxylic acid, m.p. 235°–238° C. (dec.). Analysis: Calculated for $C_{18}H_{17}FN_2O_5$: %C, 60.0; %H, 4.7; %N, 7.8; Found: %C, 59.9, %H, 4.8; %N, 8.0. The structural assignment was confirmed by infrared and nuclear magnetic resonance spectral analyses.

EXAMPLE 11

A mixture of 50 ml of 6 N hydrochloric acid and 1.8 g of ethyl 8-acetamidomethyl-6,7-dihydro-5-methyl-1-oxo-1H,5H-benzo[ij]quinolizine-2-carboxylate was heated at reflux for two hours, then evaporated to dryness. The residue was dissolved in 50 ml of water and 5 ml of formaldehyde (37%), and 1 g of 10% palladium on charcoal was added. The mixture was hydrogenated on a Paar apparatus at 50 psi at 50° C. for 24 hours. The mixture was filtered and evaporated to dryness. The residue was dissolved in 50 ml of water. One ml of 3 N hydrochloric acid was added and the mixture was cooled, then filtered. The filtrate was concentrated to 10 ml, and 30 ml of hot isopropyl alcohol was added. The precipitate obtained on cooling was white crystals of 6,7-dihydro-8-(N,N-dimethylaminomethyl)-5-methyl-1-oxo-1H,5H-benzo[ij]quinolizine-2-carboxylic acid hydrochloride, m.p. >300° C. Analysis: Calculated for $C_{17}H_{20}N_2O_3 \cdot HCl$: %C, 60.6; %H, 6.3; %N, 8.3; Found: %C, 60.2; %H, 6.2; %N, 8.2. The structural assignment was confirmed by infrared and nuclear magnetic resonance spectral analyses.

EXAMPLE 12

A mixture of 20 ml of 97% formic acid and 10 ml of acetic anhydride was heated on a steam bath for five minutes, followed by the addition of 2.0 g of 8-amino-6,7-dihydro-9-fluoro-5-methyl-1-oxo-1H,5H-benzo[ij]-quinolizine-2-carboxylic acid. Heating was continued for 15 minutes, then the mixture was evaporated to dryness. The residue was triturated with water and the solid obtained was recrystallized from 25 ml of glacial acetic acid. The product was 6,7-dihydro-9-fluoro-8-formamido-5-methyl-1-oxo-1H,5H-benzo[ij]quinolizine-2-carboxylic acid, m.p. 285° C. (dec.). Analysis: Calculated for $C_{15}H_{13}FN_2O_4 \cdot \frac{1}{2}CH_3CO_2H$: %C, 57.5; %H, 4.5; %N, 8.3; Found: %C, 57.5; %H, 4.2; %N, 8.0. The structural assignment was confirmed by infrared and nuclear magnetic resonance spectral analyses.

EXAMPLE 13

A solution of 1.0 g of 8-aminomethyl-6,7-dihydro-5-methyl-1-oxo-1H,5H-benzo[ij]quinolizine-2-carboxylic acid in 30 ml of glacial acetic acid was mixed with 0.5 g of succinic anhydride and heated at reflux for two hours. Evaporation provided a residue which was dissolved in water. Isopropyl alcohol was added, and after three weeks a white crystalline product, 6,7-dihydro-5-methyl-1-oxo-8-succinimidomethyl-1H,5H-benzo[ij]-quinolizine-2-carboxylic acid hydrate, was obtained, m.p. 265° C. (dec.) Analysis: Calculated for $C_{19}H_{18}N_2O_5 \cdot \frac{1}{4}H_2O$: %C, 63.5; %H, 5.2; %N, 7.8; Found: %C, 63.7; %H, 5.1; %N, 7.6. The structural assignment was confirmed by infrared and nuclear magnetic resonance spectral analyses.

EXAMPLE 14

Preparation of
8-cyano-6,7-dihydro-5-methyl-1-oxo-1H,5H-benzo[ij]-quinolizine-2-carboxylic acid Step A To 250 ml of hot 48% fluoroboric acid was added 50 g of 8-amino-6,7-dihydro-5-methyl-1-oxo-1H,5H-benzo[ij]quinolizine-2-carboxylic acid. The solution was gradually cooled to 0° C., and 16.8 g of sodium nitrite in 50 ml of water was added slowly with vigorous stirring. After stirring about 30 minutes at 0° C., 250 ml of an ice water mixture was added. Stirring was continued for about thirty minutes. The solid was separated by filtration and washed sequentially with an isopropanol-fluoroboric acid mixture (50/50), isopropanol, an isopropanol-diethyl ether mixture (50/50), and diethyl ether. The product, 8-diazonium-6,7-dihydro-5-methyl-1-oxo-1H,5H-benzo[ij]quinolizine-2-carboxylic acid fluoroborate, was a gold solid.

Step B

A mixture of 81 g of cuprous cyanide and 57 g of sodium cyanide in 550 ml of dimethyl sulfoxide was heated on a steam bath until the solids were dissolved. After cooling to 25° C., 55 g of 8-diazonium-6,7-dihydro-5-methyl-1-oxo-1H,5H-benzo[ij]quinolizine-2-carboxylic acid fluoroborate from Step A in 275 ml of dimethyl sulfoxide was added slowly with rapid stirring. The temperature was maintained below 30° C. for one hour after the completion of the addition. The mixture was then poured into 5 liters of water. The tan solid was separated by filtration and recrystallized from N,N-dimethylformamide to provide 8-cyano-6,7-dihydro-5-methyl-1-oxo-1H,5H-benzo[ij]quinolizine-2-carboxylic acid, m.p. >300° C. Analysis: Calculated for $C_{15}H_{12}N_2O_3$: %C, 67.2; %H, 4.5; %N, 10.4; Found: %C, 67.1; %H, 4.8; %N, 10.1.

EXAMPLE 15

Preparation of
8-cyano-6,7-dihydro-9-fluoro-5-methyl-1-oxo-1H,5H-benzo[ij]quinolizine-2-carboxylic acid Part A To a mixture of 225 ml (3.75 mole) of concentrated sulfuric acid and 225 ml (3.3 mole) of concentrated nitric acid was added 100 g (0.713 mole) of 2-fluorobenzoic acid. The temperature was maintained between 15° and 25° C. The mixture was stirred for an hour after completion of the addition. The temperature rose to about 30° C. The solution was decanted into 4 liters of ice water to provide 111.1 g of white crystals of 2-fluoro-5-nitrobenzoic acid. The structural assignment was confirmed by infrared and nuclear magnetic resonance spectral analyses.

Part B 111 g of 2-fluoro-5-nitrobenzoic acid was dissolved in 1 liter of ethyl acetate. To this solution was added 5 g of 5 percent palladium on charcoal. The mixture was hydrogenated on a Parr apparatus for 24 hours at 20° C. at 50 psi of hydrogen. The theoretical amount of hydrogen was absorbed. The solution was filtered, then evaporated to dryness to provide a tan residue of 95.2 g of 5-amino-2-fluorobenzoic acid.

Part C

A mixture of 95.2 g of 5-amino-2-fluorobenzoic acid, 74.3 g (0.33 mole) of sodium meta-nitrobenzenesulfonic acid, 46.2 g of ferrous sulfate heptahydrate and 660 ml of 9 N hydrochloric acid was heated to 90°–95° C. Crotonaldehyde (96%) 77 g, 1.0 mole, was added dropwise over 2.5 hours with good stirring maintaining a temperature just below reflux. After stirring an additional half hour, the solution was filtered hot through a glass wool plug. The filtrate was cooled to 30° C. and treated with decolorizing charcoal and filtered. The clear filtrate was cooled in ice with stirring to provide a light yellow solid. The solid was separated by filtration, washed with acetone and dried. The solid was dissolved in 400 ml of hot water and a solution of 50 g of sodium acetate in 100 ml of water was added. The product obtained was separated by filtration and dried. The product was 58.2 g of cream-colored crystals of 5-carboxyl-6-fluoroquinaldine. The structural assignment was confirmed by infrared and nuclear magnetic resonance spectral analyses.

Part D

A mixture of 58.2 g of 5-carboxyl-6-fluoroquinaldine and 200 ml of thionyl chloride with 2.5 ml of N,N-dimethylformamide was heated on a steam bath for 10 minutes. The mixture was allowed to sit at 20° C. for 0.5 hour, then 400 ml of diethyl ether was added. The white solid precipitate was separated by filtration, washed with diethyl ether and dried. This product was the acyl chloride derivative. This product was added in small portions to 200 ml of cold concentrated ammonium hydroxide with rapid stirring. The mixture was stirred for 20 minutes at 20° C. The product was separated by filtration, washed with water and dried to provide 49 g of 5-carboxamido-6-fluoroquinaldine. The structural assignment was confirmed by infrared and nuclear magnetic resonance spectral analyses.

Part E

To a mixture of 49 g of 5-carboxamido-6-fluoroquinaldine, 44.5 ml of pyridine and 250 ml of dichloromethane was added 37 ml of trifluoroacetic anhydride, while maintaining the temperature between 24° and 27° C. This addition required about 6 hours. The solution was stirred at 20° C. for 16 hours, then 100 ml of 1 N cold sodium hydroxide solution was added. The layers were separated, and the organic layer was washed with water and then dried over magnesium sulfate. The organic solution was then evaporated and the residue was triturated with water to provide a tan solid. The solid was separated by filtration and washed with water to provide 42.2 g of 5-cyano-6-fluoroquinaldine. The structural assignment was confirmed by infrared spectral analysis.

Part F

A solution of 42.2 g of 5-cyano-6-fluoroquinaldine and 150 ml of glacial acetic acid and 150 ml of isopropyl alcohol was formed by heating. The mixture was cooled to about 35° C. and 7.5 g of sodium acetate and 3 g of 5% platinum on carbon were added. The mixture was hydrogenated on a Paar apparatus for 72 hours at 30 psi. The theoretical amount of hydrogen was 41 psi, the actual hydrogen absorbed was 43 psi. The catalyst was separated by filtration and the filtrate was evaporated to provide an oil. Ice water was added. The pH of the mixture was adjusted to 8 with sodium hydroxide and sodium bicarbonate. The solid product was separated by filtration and washed with water, then dried. The product was 5-cyano-6-fluorotetrahydroquinaldine (40.2 g of cream crystals). The structural assignment was confirmed by infrared spectral analyses.

Part G

A mixture of 40.2 g of 5-cyano-6-fluorotetrahydroquinaldine and 69 g of diethyl ethoxymethylenemalonate in 300 ml of xylene was heated at its reflux temperature for 28 hours using a Dean Stark trap to remove xylene. The xylene removed was replaced with equal volumes of fresh xylene. After this reaction period the reaction mixture was evaporated to 250 ml volume. To this solution was added 500 ml of heptane. The solution was filtered and the filtrate was treated with 350 ml of hexane. On cooling and stirring, cream crystals of the desired condensation product were obtained. The product was washed with a xylene/hexane (1:4) mixture and then with hexane to provide 58.3 g of product. The structural assignment was confirmed by infrared and nuclear magnetic resonance spectral analyses.

Part H

A portion of the product from Part G, 5.0 g, was combined with 15 g of polyphosphoric acid and the mixture was heated at 140° C. for 45 minutes with stirring. The mixture was cooled, and 75 ml of water was added. The mixture was stirred for 30 minutes then the white solid product 8-cyano-6,7-dihydro-9-fluoro-5-methyl-1-oxo-1H,5H-benzo[ij]quinolizine-2-carboxylic acid as the ethyl ester was obtained. Infrared and nuclear magnetic spectral analyses of this product indicated that the cyano group in the 8-position has been partially hydrolyzed back to the carboxamido group. That is, the desired product was mixed with ethyl 8-carboxamido-6,7-dihydro-9-fluoro-5-methyl-1-oxo-1H,5H-benzo[ij]quinolizine-2-carboxylate.

Part I

The product from Part H, 4.2 was suspended in 250 ml of dichloromethane and 4.8 ml of pyridine. To the stirred mixture was added, over 10 minutes, 4 ml of trifluoroacetic anhydride. The solution was stirred for three hours, then washed with cold 3% sodium hydroxide solution. The solution was dried over magnesium sulfate, treated with decolorizing charcoal and evaporated. The white residue was recrystallized from aqueous N,N-dimethylformamide to provide 2.4 g of white needles of ethyl 8-cyano-6,7-dihydro-9-fluoro-5-methyl-1-oxo-1H,5H-benzo[ij]quinolizine-2-caboxylate, m.p. 260°–263° C. Analysis: Calculated for $C_{17}H_{15}FN_2O_3$; %C, 65.0; %H, 4.8; %N, 8.9; Found: %C, 64.4; %H, 4.8; %N, 8.8. The structural assignment was confirmed by infrared spectral analysis.

Part J

A solution of 2.0 g of the product of Part I and 35 ml hot glacial acetic acid was treated with 40 ml of 3 N hydrochloric acid and the mixture was heated at reflux temperature for 1 hour. The mixture was cooled and filtered, and the solid was washed with water to provide 1.7 g of 8-cyano-6,7-dihydro-9-fluoro-5-methyl-1-oxo-1H,5H-benzo[ij]quinolizine-2-carboxylic acid as a white solid, m.p. 300° C. Analysis: Calculated for $C_{15}H_{11}FN_2O_3$: %C, 62.9; %H, 3.8; %N, 9.8; Found: %C, 62.5; %H, 3.4; %N, 9.7.

EXAMPLE 16

A solution of 4.0 g (10.6 mmole) of 6,7-dihydro-5-methyl-1-oxo-8-phenylureido-1H,5H-benzo[ij]quinolizine-2-carboxylic acid and 0.4 g (10 mmole) sodium hydroxide in 150 ml of water was prepared by warming the mixture. The solution was filtered, then lyophilized to provide an off-white solid, sodium 6,7-dihydro-5-methyl-1-oxo-8-phenylureido-1H,5H-benzo[ij]quinolizine-2-carboxylate hydrate, m.p. 270° C. (dec.). Analysis: Calculated for $C_{21}H_{18}N_3NaO_4 \cdot \frac{1}{2}H_2O$: %C, 59.2; %H, 4.5; %N, 9.9; Found: %C, 59.0; %H, 4.8; %N, 9.9. The structural assignment was confirmed by infrared and nuclear magnetic resonance spectral analyses.

What is claimed is:

1. A compound of the formula

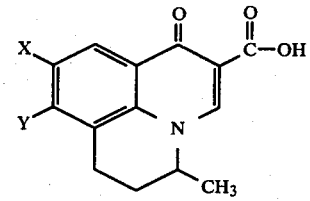

wherein X is hydrogen or fluorine; Y is selected from the group consisting of

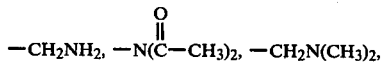

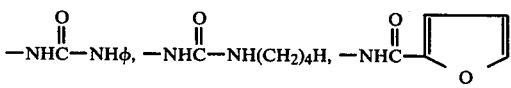

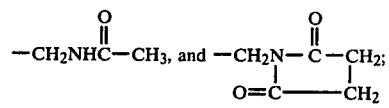

or an alkyl or aminoalkyl ester thereof having one to four carbon atoms in the alkyl group, an aminoalkyl ester salt thereof having one to four carbon atoms in the alkyl group or a pharmaceutically-acceptable carboxylate salt thereof.

2. The compound according to claim 1 selected from the group consisting of (1) where X is hydrogen and Y is

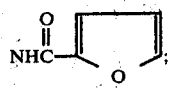

(2) where X is hydrogen and Y is —CH$_2$NH$_2$; (3) where X is hydrogen and Y is

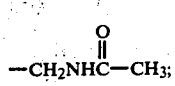

(4) where X is fluoro and Y is

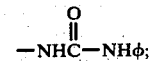

(5) where X is fluoro and Y is

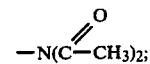

and (6) where X is hydrogen and Y is —CH$_2$N(CH$_3$)$_2$.

3. The compound according to claims 1 or 2 which is a carboxylic acid.

4. A composition for inhibiting the growth of microorganisms comprising an effective amount of a compound according to claims 1 or 2 formulated in a pharmaceutically-acceptable vehicle.

5. A method of inhibiting the growth of microorganisms comprising contacting said microorganisms with an effective amount of a compound according to claims 1 or 2.